(12) United States Patent
McKinsey et al.

(10) Patent No.: US 8,597,342 B2
(45) Date of Patent: Dec. 3, 2013

(54) TEXTILE GRAFT FOR IN SITU FENESTRATION

(75) Inventors: James F. McKinsey, West Harrison, NY (US); Shyam S V Kuppurathanam, Bloomington, IN (US); Matthew S. Waninger, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 837 days.

(21) Appl. No.: 12/195,762

(22) Filed: Aug. 21, 2008

(65) Prior Publication Data

US 2009/0157164 A1 Jun. 18, 2009

Related U.S. Application Data

(60) Provisional application No. 60/957,801, filed on Aug. 24, 2007.

(51) Int. Cl.
*A61F 2/06* (2013.01)

(52) U.S. Cl.
USPC .................. 623/1.13; 623/1.15; 623/1.51

(58) Field of Classification Search
USPC .......... 623/1.15, 1.35, 1.32, 1.34, 1.49, 1.5, 623/1.51, 1.53, 1.54, 1.13
See application file for complete search history.

(56) References Cited

U.S. PATENT DOCUMENTS

| | | | |
|---|---|---|---|
| 5,617,878 A | 4/1997 | Taheri | |
| 5,755,772 A | 5/1998 | Evans et al. | |
| 5,961,548 A | 10/1999 | Shmulewitz | |
| 6,161,399 A | 12/2000 | Jayaraman | 66/170 |
| 6,652,567 B1 | 11/2003 | Deaton | |
| 6,792,979 B2 | 9/2004 | Konya et al. | 140/92.1 |
| 6,814,754 B2 | 11/2004 | Greenhalgh | 623/1.51 |
| 2002/0034902 A1 | 3/2002 | Litton | 442/92 |
| 2002/0052649 A1* | 5/2002 | Greenhalgh | 623/1.35 |
| 2003/0204235 A1 | 10/2003 | Edens et al. | 623/1.5 |
| 2004/0215320 A1 | 10/2004 | Machek | 623/1.13 |
| 2005/0154444 A1 | 7/2005 | Quadri | 623/1.13 |
| 2005/0187604 A1 | 8/2005 | Eells et al. | 623/1.13 |
| 2005/0240261 A1 | 10/2005 | Rakos et al. | 623/1.51 |
| 2006/0009835 A1 | 1/2006 | Osborne et al. | 623/1.13 |
| 2006/0019561 A1 | 1/2006 | Schindzielorz et al. | 442/59 |
| 2006/0024496 A1 | 2/2006 | Hietpas et al. | 428/359 |

* cited by examiner

*Primary Examiner* — Thomas J Sweet
*Assistant Examiner* — Matthew Schall
(74) *Attorney, Agent, or Firm* — Brinks Gilson & Lione

(57) ABSTRACT

The disclosure relates to an implantable woven graft for bridging a defect in a main vessel near one or more branch vessels. The graft includes a region of reduced yarn density. Reduced yarn density regions are alignable with at least one of the one or more branch vessels, and are suitable for in situ fenestration, for example by perforation. The disclosed examples are particularly suited for bridging abdominal aortic aneurysms.

20 Claims, 5 Drawing Sheets

TEXTILE GRAFT FOR IN SITU FENESTRATION

PRIORITY CLAIM

This application claims the benefit of provisional U.S. Patent Application Ser. No. 60/957,801, filed Aug. 24, 2007, which is incorporated herein by reference in its entirety.

BACKGROUND OF THE INVENTION

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

In many cases, however, the damaged or defected portion of the vasculature may include a branch vessel. For example, in the case of the abdominal aorta, there are at least three branch vessels, including the celiac, mesenteric, and renal arteries, leading to various other body organs. Thus, when the damaged portion of the vessel includes one or more of these branch vessels, some accommodation must be made to ensure that the stent graft does not block or hinder blood flow through the branch vessel.

A common method to provide continued blood flow to branch vessels includes by-pass vessels surgically located in an undamaged region of the aorta that is not stented. Such invasive methods, however, are undesirable. A less invasive technique to provide continued blood flow to branch vessels includes the placement of holes or fenestrations in the stent graft that are aligned with the side branch vessel so as to allow blood to continue to flow into the side branch vessel. The fenestration approach is the preferred method since it does not involve major vascular surgery. However, inaccuracies in the location of fenestrations may occur due to the unique vasculature and location of branch vessels in each patient.

SUMMARY

In one example, an implantable graft is provided. The implantable graft comprises a main graft body forming a lumen with a proximal end and a distal end. At least a portion of the lumen is defined by a woven fabric having yarns aligned in a first direction interwoven with yarns aligned in a second direction. The woven fabric includes a main portion and at least one reduced yarn density region disposed between the proximal and distal end. Although at least some yarns traverse the reduced yarn density region, the reduced yarn density region is defined by having a lower yarn density than the main portion. Preferably, the reduced yarn density region has between about 65% and about 95% fewer yarns aligned in the first direction than the main portion.

In another example, an implantable prosthesis for treatment of a main vessel defect near one of more branch vessels is provided. The prosthesis comprises a graft having yarns aligned in a first direction interwoven with yarns aligned in a second direction. The woven yarns define a lumen with a proximal end and a distal end, a main portion and at least one passage disposed between the proximal and distal end. Although at least some yarns traverse the passage, the passage is defined by having a lower yarn density than the main portion. In some examples, the implantable prosthesis further includes at least two stents attached to the graft, one of which is attached between the distal end and the passage, the other of which is attached between the proximal end and the passage.

In a further example, a method of bridging a defect in a main vessel near at least one branch vessel is provided. The method comprises providing a prosthesis comprising at least one stent and an implantable textile graft comprising yarns aligned in a first direction interwoven with yarns aligned in a second direction, the woven yarns defining a lumen with a main portion and at least one reduced yarn density region. The reduced yarn density region has a yarn density lower than the main portion. The prosthesis is deployed into the main vessel of a patient in need thereof, such that a reduced yarn density region is aligned with a branch vessel. The reduced yarn density region may be perforated to define a passageway from the main vessel to the at least one branch vessel.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

Figure 1:
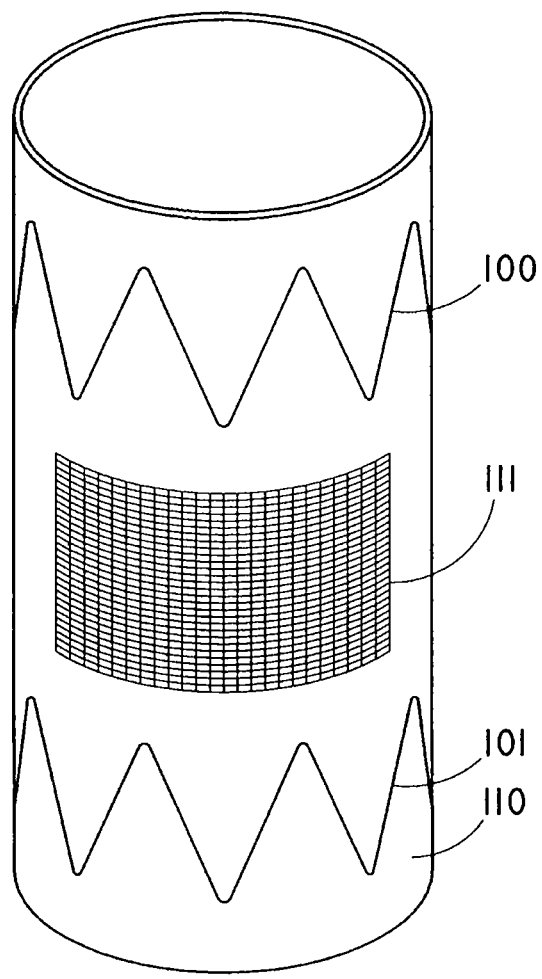
FIG. 1 is a perspective illustration of one example of a woven textile according to the present disclosure.

The present disclosure provides for a variable yarn density textile graft for bridging a defect in a main vessel near one or more branch vessels. Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, billiary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis.

The term "stent graft" as used herein refers to a prosthesis comprising a stent and a graft material associated therewith that forms a lumen through at least a portion of its length.

"Proximal" means that position or portion of a component which is closest to the patient's heart.

"Distal" means that position of portion of a component which is furthest from the patient's heart.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Variable Yarn Textile Grafts

Variable yarn density textile grafts include any prosthesis that is introduced temporarily or permanently into the body for the prophylaxis or therapy of a medical condition. Typical subjects (also referred to herein as "patients") are vertebrate subjects (i.e., members of the subphylum cordata), including, mammals such as cattle, sheep, pigs, goats, horses, dogs, cats and humans. Variable yarn density textile grafts of the present disclosure comprise at least one region of reduced yarn density permitting in situ fenestration.

For example, FIG. 1 depicts one example of a segment of an illustrative stent graft comprising stents 100, 101 and variable yarn density textile graft 110. Textile graft 110 comprises a region of reduced yarn density 111. In one example, stents are located adjacent the reduced yarn density graft region 111 for support and rigidity. For example, stents may be distal 101 and proximal 100 the reduced yarn density region 111.

Figure 2:
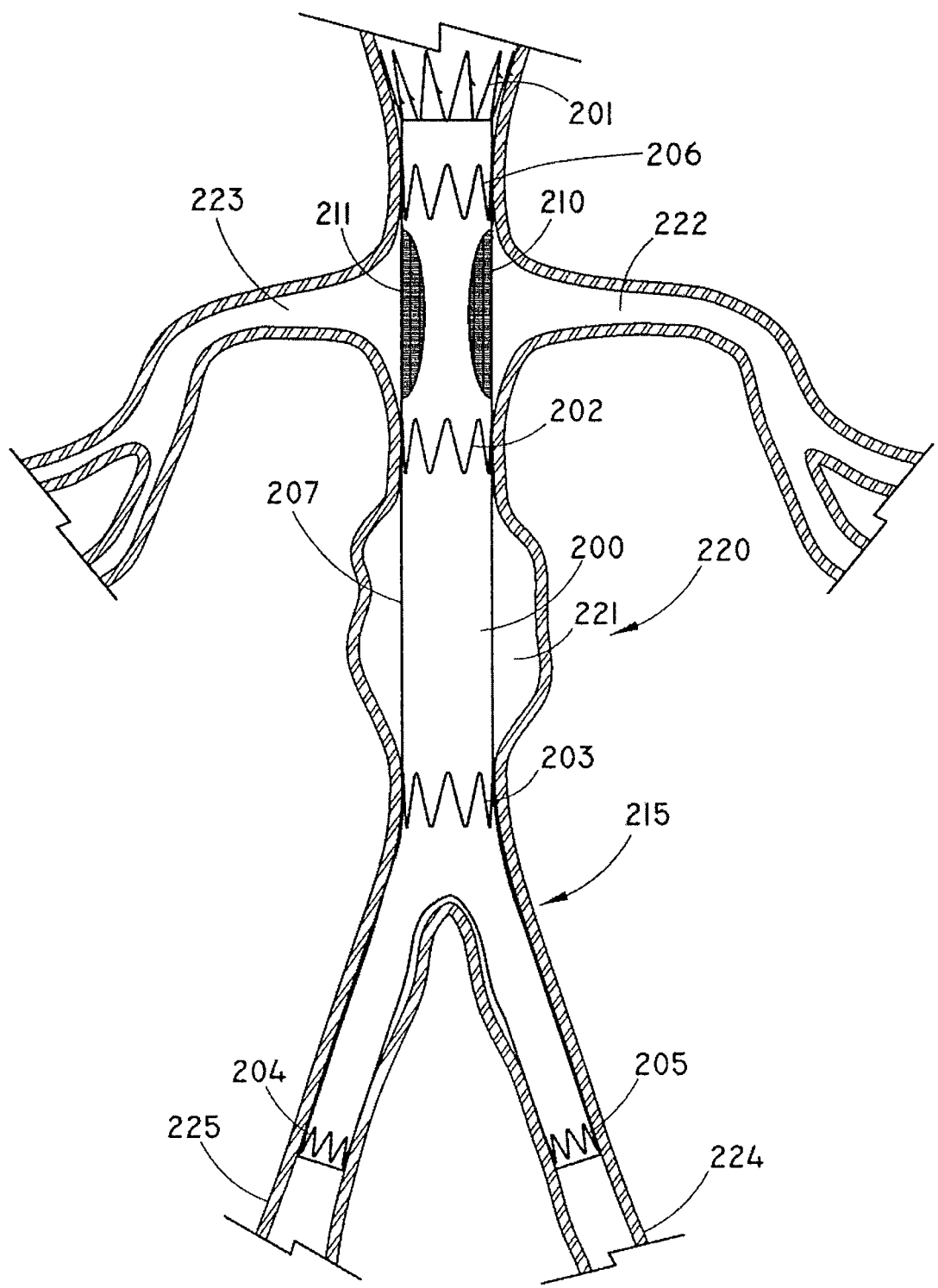
FIG. 2 depicts an abdominal aorta with a woven textile graft having reduced yarn density regions aligned with the renal arteries.

The reduced yarn density region of the textile graft is preferably aligned with a branch vessel upon implantation. For example, FIG. 2 illustrates an aortic stent graft 200 comprising a main portion 207 and two reduced yarn density regions 210, 211 aligned with the renal arteries 222, 223. The aorta 220 has an aneurysm 221 between the renal arteries 222, 223 and the iliac arteries 224, 225. Upon implantation, the reduced yarn density graft regions 210, 211 are aligned with the renal arteries 222, 223, respectively. The reduced yarn density regions may be perforated, preferably in situ, to establish fenestrations providing blood flow to the real arteries 222, 223.

For example, in situ fenestrations may be created about the reduced yarn density regions to permit blood flow therethrough by any suitable means, including, but not limited to, the insertion of a guide wire, balloon, and/or stent to perforate the reduced yarn density region. In one example, a graft comprising a reduced yarn density region may be delivered and positioned at a desired location within a patient's vasculature via a guide wire. Following proper positioning of the graft, the guide wire may be used to poke through and perforate the reduced yarn density region. In some examples, an inflatable balloon may be used to enhance perforation of the reduced yarn density region to further enable blood flow through the fenestration.

Figure 3:
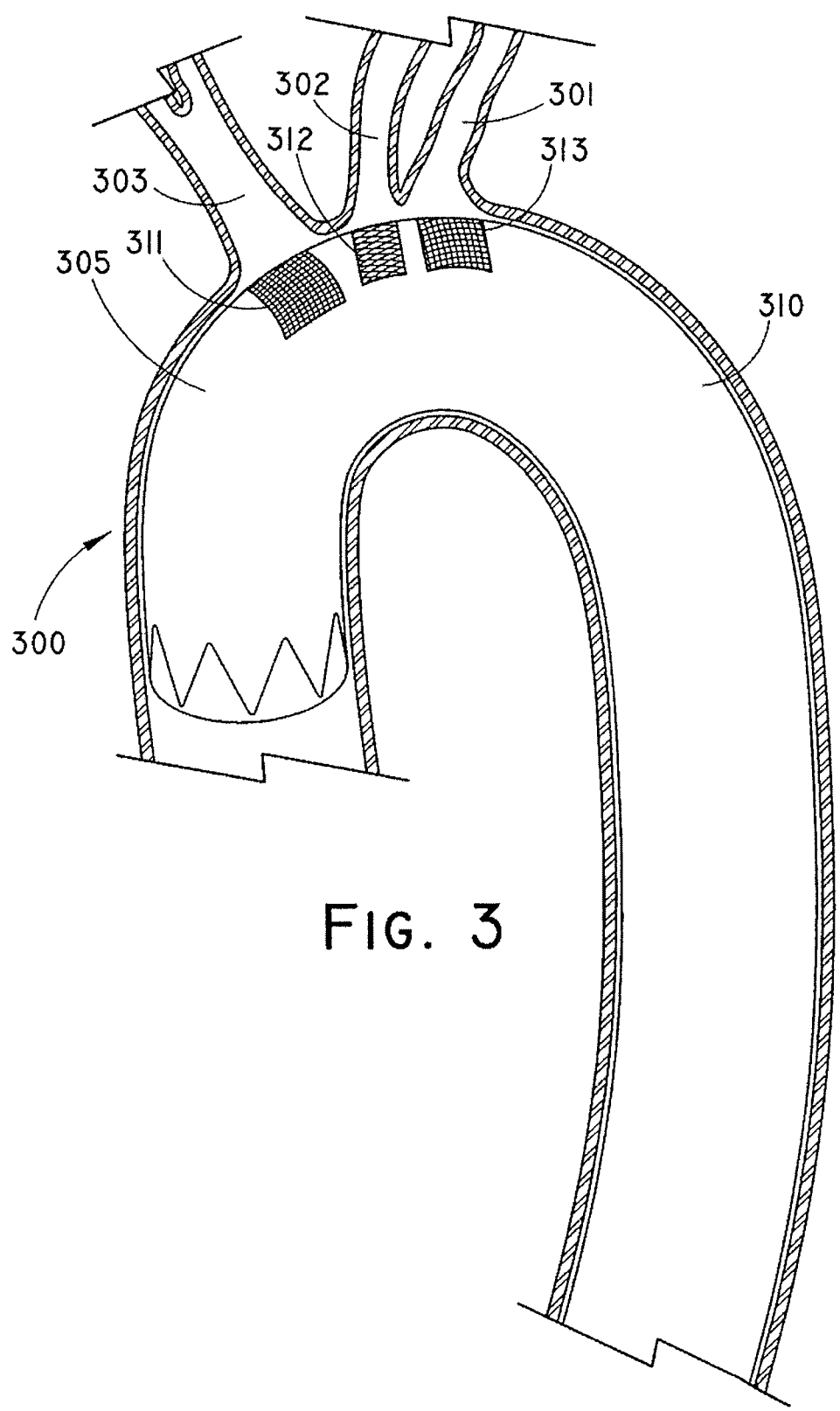
FIG. 3 depicts a woven textile graft positioned in the thoracic aorta and having reduced yarn density regions aligned with the cranial arteries.
Figure 4:
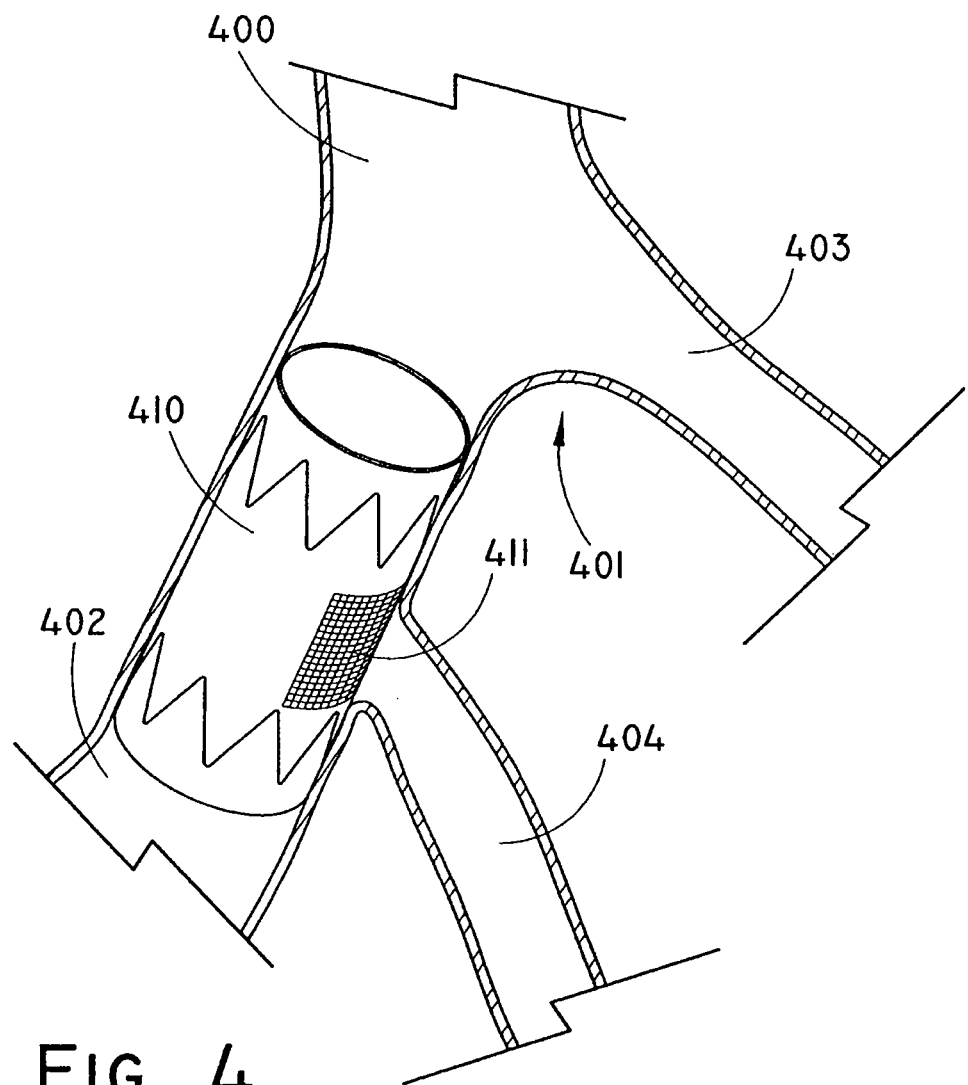
FIG. 4 is a partial illustration of the abdominal aorta with a woven textile graft according to the present disclosure placed in the iliac artery and having a reduced yarn density region aligned with the hypogastric artery.

FIGS. 3 and 4 further illustrate stent grafts having reduced yarn density regions aligned with various vessels that branch off the aorta. For example, FIG. 3 illustrates a textile graft 310, implanted within the thoracic aorta 300, having a main graft portion 305 and reduced yarn density regions 311, 312, 313 aligned with the left subclavian artery 301, the left common carotid artery 302, and the brachiocephalic trunk 303. FIG. 4 is a partial illustration of an aortic vessel 400 at the point of bifurcation 401 into the iliac arteries 402, 403. As depicted, a stent graft 410 having a generally tubular shape is implanted within the left iliac artery 402 with a reduced yarn density region 411 aligned with the hypogastric artery 404.

Though the above examples illustrate grafts located within the aorta, prostheses of the present disclosure may be implanted in any body vessel, including main vessels in which one or more branch vessels may be located. Though reduced yarn density regions in the illustrative figures above are shown with rectangular or round shapes, the shape and size of the reduced yarn density region may be any appropriate size and shape. For example, the reduced yarn density region may comprise a square shape, a polygonal shape, or be free-form. Furthermore, the reduced yarn density region may have any suitable length and width. For example, the reduced yarn density region may have a width which is less than the circumferential width (e.g., partial circumference) or be circumferentially around the textile graft.

Graft Weaves

The graft may comprise any kind of suitable weave or weaves. For example, the textile graft may include, but is not limited to, weaves such as plain weaves, modified plain weaves, basket weaves, rep or rib weaves, twill weaves (e.g., straight twill, reverse twill, herringbone twill), modified twill weaves, satin weaves, double weaves (e.g., double-width, tubular double weave, reversed double weave), and any other related weaves. The reduced yarn density region of the textile graft may comprise a similar weave or a different weave pattern from the remainder of the textile graft. In one example, the textile graft comprises a single weave pattern for both the main portion and reduced yarn density region. In another example, the textile graft comprises two or more weave patterns for the main portion and reduced yarn density region of the textile graft.

The graft reduced yarn density region may be woven, for example, by dropping and adding yarns, by fast/slow take-up, and by having more than one weave designs. In one example, the textile graft comprises a plain weave having 150 ends per inch and 250 picks per inch. An "end" refers to an individual warp yarn, and "sett" is the number of warp yarns per inch in a woven fabric. A "pick" refers to an individual weft yarn, and "pick count" is the number of weft yarns per inch in a woven fabric. The reduced yarn density region also comprises a plain weave having 150 ends per inch. To be susceptible to perforation, the reduced yarn density region pick count is less than 150, allowing the region to have a yarn density less than that of the remainder of the textile graft.

Preferably, the reduced yarn density region pick count is between about 10% to about 90% of the pick count of the main portion of the textile graft. Even more desirably, the reduced yarn density region pick count is between about 15% to about 30% of the main portion textile graft pick count.

In another example, the sett may be reduced in the textile graft reduced yarn density region as compared to the main portion of the textile graft. Desirably, the reduced yarn density region sett is between about 10% to about 90% of the main portion of the textile graft. Even more desirably, the reduced yarn density region sett is between 15% to about 35% of the main portion of the textile graft.

The reduced yarn density region pick count and sett may vary depending on a number of factors, including intended use of the textile graft, the selected weave or weaves, and the yarn density of the remainder of the textile graft. In one example, the reduced yarn density region may include a variable weave density. For example, the reduced yarn density region may have a higher weave density about the circumference of the reduced yarn density region and progressively lessen as the weave approaches the center of the reduced yarn density region. A reduced yarn density region variable weave the may permit a tighter fit between a bridge stent and a fenestration, thereby decreasing any fluid leakage about the circumference of the fenestration.

The reduced yarn density region may have any suitable shape, including but not limited to round, obround, polygonal, rectangular, square, or freeform, or combinations thereof. In one example, the reduced yarn region may be woven in a circular fashion, thereby permitting a bridge stent to better conform to the resulting fenestration.

Graft Material

The graft material may comprise any biocompatible material suitable for weaving. The graft material may be natural, synthetic, or manufactured. For example, biocompatible materials include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile graft, provided the final textile is biocompatible.

Polymeric materials suitable for weaving graft material include polyethylene, polypropylene, polyaramids, polyacrylonitrile, nylons and cellulose, in addition to polyesters, fluorinated polymers, and polyurethanes as listed above. Desirably, the textile graft material comprises one or more polymers that do not require treatment or modification to be biocompatible. More desirably, the textile graft material comprises biocompatible polyesters. Even more desirable, textile graft material comprises polyethylene terephthalate and PTFE. A preferred commercial example of polyethylene terephthalate especially suitable for weaving is Dacron. These materials are inexpensive, easy to handle, have good physical characterstics and are suitable for clinical application.

The graft material may be woven of a single material or combination of materials. Determination of which combination of materials woven in which direction of the textile graft that is most appropriate may be based on the type of clinical application, properties of the textile graft that are desired, and further factors such as the weave type, yarn properties such as the size or denier of the yarn, finishing techniques, and/or permeability of the textile. For example, for percutaneous application, thin textile grafts are preferred. Such thin grafts comprise yarns that have are fine or have a low denier. Desirably, textile graft yarns range in size from about 0.1 denier to about 200 denier.

Stents

One or more stents may be attached or adhered to the textile graft by any suitable means, including but not limited to welding, stitching, bonding, and adhesives. In one example, stents may be sutured to the textile graft. In general, stents for use in connection with the present disclosure typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

In one example, stents may be located distal and proximal to a reduced yarn density region. For example, in FIG. 1, stent 100 is located proximal, or upstream, from reduced yarn density region 111, and stent 101 is located distal to the region 111. Stents located distal and proximal to a reduced yarn density region provide structure and rigidity to the textile graft. Additionally, proximal and distal stents may seal against the main vessel wall to prevent leakage around a branch vessel following perforation.

In another example, stents are located at the proximal and distal ends of the textile graft. For example, in FIG. 2, stents are located at the proximal 201, 206 and distal 204, 205 textile graft ends. Textile graft proximal 201 and distal stents 204, 205 may seal against the main vessel wall 215 to prevent undesirable fluid leakage, for example by reducing blood leakage into an aneurysmal sac 221 spanned by an implanted textile graft. Additional stents 202, 203 may further aid in sealing against the vessel wall 215 to prevent undesirable fluid leakage into the aneurysmal sac 221.

The stents may be self-expanding or balloon-expandable, and may be deployed according to conventional methodology, such as by an inflatable balloon catheter, by a self-deployment mechanism (after release from a catheter), or by other appropriate means. The stents may be bifurcated, configured for any blood vessel including coronary arteries and peripheral arteries (e.g., renal, superficial femoral, carotid, and the like), a urethral stent, a biliary stent, a tracheal stent, a gastrointestinal stent, or an esophageal stent, for example. Desirably, the stent is a vascular stent such as the commercially available Gianturco-Roubin FLEX-STENT®, GRII™, SUPRA-G, or V FLEX coronary stents from Cook Incorporated (Bloomington, IN).

The stents may be made of one or more suitable biocompatible materials such as stainless steel, nitinol, MP35N, gold, tantalum, platinum or platinum irdium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or nitinol.

Radiopacity

Also provided are examples where the textile graft comprises a means for orienting the graft within a body lumen. For example, reduced yarn density textile graft regions may be marked for radiographic visualization to facilitate precise alignment of each reduced yarn density region with the particular branch anatomical conduit (e.g., carotid, innominate, subclavian, intercostal, superior mesenteric, celiac, renal, iliac, hypogastric, or visceral vessels). Radiopaque portions of the textile graft would be seen by remote imaging methods including X-ray, ultrasound, Magnetic Resonance Imaging and the like, or by detecting a signal from or corresponding to the marker.

Figure 5A:
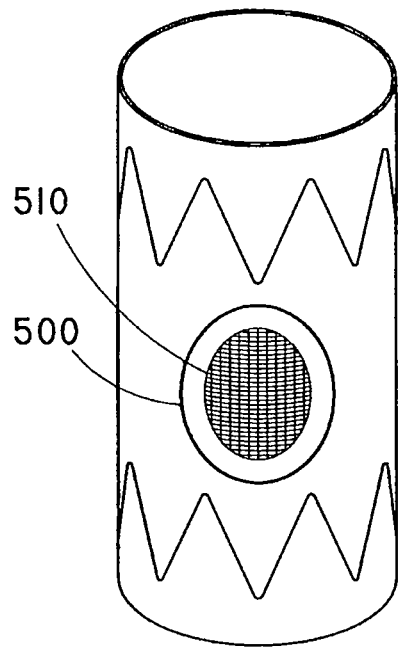
FIGS. 5A and 5B are perspective illustrations of woven grafts having radiopaque markers about a reduced yarn density region.
Figure 5B:
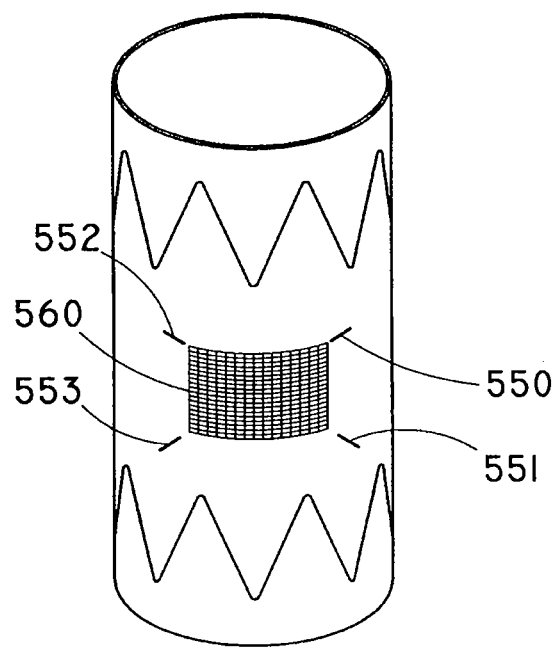

FIGS. 5A and 5B illustrate various examples comprising radiopaque markers to facilitate tracking and positioning of the textile graft. In FIG. 5A, a radiopaque ring 500 circumscribes the textile graft reduced yarn density region 510. FIG. 5B illustrates four radiopaque markers 550, 551, 552, 553 located adjacent a reduced yarn density region 560. Alternatively, stents located proximal and distal a reduced yarn density region may comprise radiopaque portions to assist in appropriately orienting the textile graft in the body vessel.

In other examples, the delivery device can comprise indicia relating to the orientation of the frame within the body vessel. In other examples, indicia can be located, for example, on a portion of a delivery catheter that can be correlated to the location of the prosthesis within a body vessel.

Radiopaque materials may be added to the textile graft by any fabrication method or absorbed into or sprayed onto the surface of part or all of the graft. The degree of radiopacity contrast can be altered by implant content. Common radiopaque materials include barium sulfate, bismuth subcarbonate, and zirconium dioxide. Other radiopaque elements include: cadmium, tungsten, gold, tantalum, bismuth, platium, iridium, and rhodium. Radiopacity is typically determined by fluoroscope or x-ray film.

Attachment of Graft in Body Vessel

Prostheses according to the present disclosure may optionally include supplemental attachment means such as anchoring members, suturing, stapling, searing, bonding, gluing, bioadhesives, or otherwise adhering the medical device to the vessel wall or combinations thereof. For example, the textile graft may be secured in place with one or more anchoring devices.

A wide variety of structural features are acceptable for use in medical devices as anchoring members, and any suitable structural feature can be used. For example, individual barbs may be used to implant the textile graft into a body vessel. The barbs may be secured to the textile graft by any means known to one skilled in the art, including but not limited to welding to included stents, stitching, bonding, and adhesives. Desirably, barbs may be attached to stents included in the prosthesis. In some examples, the number, arrangement, and configuration of barbs can vary according to design preference and the clinical use of the textile graft. The barbs can have any suitable shape, including points or "fish hook"-like configurations. The barbs may or may not penetrate the vessel wall, depending on their design and other factors.

Alternatively or in addition to anchoring members, bioadhesives may be used for attachment. Bioadhesive may be included in any suitable part of the prosthesis. Preferably, the bioadhesive is attached to the abluminal surface of the textile graft. Selection of the type of bioadhesive, the portions of the prosthesis comprising the bioadhesive, and the manner of attaching the bioadhesive to the prosthesis can be chosen to perform a desired function upon implantation. For example, the bioadhesive can be selected to promote increased affinity of the desired portion of prosthesis to the section of the body vessel against which it is urged.

Bioadhesives for use in conjunction with the present disclosure include any suitable bioadhesives known to those of ordinary skill in the art. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta(TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinyl-pylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

Furthermore, commercially available bioadhesives that may be used in the present disclosure include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGENTM produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYLTM (N-butyl cyanoacrylate), NEXABONDTM, NEXABONDTM S/C, and TRAUMASEALTM (product based on cyanoacrylate) produced by Closure Medical (TriPoint Medical); DERMABOND® which consists of 2-octyl cyanoacrylate produced as DERMABOND® by (Ethicon); TISSUE-GLU®) produced by Medi-West Pharma; and VETBOND®) which consists of n-butyl cyanoacrylate produced by 3M.

Bioactive Agents

Optionally, the textile graft can include one or more bioactive agents. The bioactive agent can be included in any suitable part of the prosthesis. The bioactive materials can be attached to the prosthesis in any suitable manner. For example, a bioactive agent may be sprayed onto the textile graft material, or stents may be dipped in bioactive agent. Selection of the type of bioactive agent, the portions of the prosthesis comprising the bioactive agent, and the manner of attaching the bioactive agent to the prosthesis can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis.

The bioactive agent can be selected to perform one or more desired biological functions. For example, the abluminal surface of the textile graft can comprise a bioactive selected to promote the ingrowth of tissue from the interior wall of a body vessel, such as a growth factor. An anti-angiogenic or antneoplastic bioactive such as paclitaxel, sirolimus, or a rapamycin analog, or a metalloproteinase inhibitor such as batimastat can be incorporated in or coated on the prosthesis to mitigate or prevent undesired conditions in the vessel wall, such as restenosis. Many other types of bioactive agents can be incorporated in the prosthesis.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-$\beta$.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Delivery of Textile Graft

The graft can be configured for delivery to a body vessel. For example, a prosthesis comprising a textile graft according to the present disclosure and stents can be compressed to a delivery configuration within a retaining sheath that is part of a delivery system, such as a catheter-based system. Upon delivery, the prosthesis can be expanded, for example, by inflating a balloon from inside the stents. The delivery configuration can be maintained prior to deployment of the prosthesis by any suitable means, including a sheath, a suture, a tube or other restraining material around all or part of the compressed prosthesis, or other methods.

Prostheses can be deployed in a body vessel by means appropriate to their design. Prostheses of the present disclosure can be adapted for deployment using conventional methods known in the art and employing percutaneous transluminal catheter devices. The prostheses are designed for deployment by any of a variety of in situ expansion means.

In one example, a prosthesis comprising self-expanding stents and a textile graft of the present disclosure may be mounted onto a catheter that holds the prosthesis as it is delivered through the body lumen and then releases the prosthesis and allows it to self-expand into contact with the body lumen. This deployment is effected after the prosthesis has been introduced percutaneously, transported transluminally and positioned at a desired location by means of the catheter. The self-expanding prosthesis may be deployed according to well-known deployment techniques for self-expanding medical devices. For example, the prosthesis may be positioned at the distal end of a catheter with a removable sheath or sleeve placed over the prosthetic valve to hold the prosthesis in a contracted state with a relatively small diameter. The prosthesis may then be implanted at the point of treatment by advancing the catheter over a guide wire to the location of the lesion, aligning reduced yarn density regions with any branch vessels, and then withdrawing the sleeve from over the prosthesis. The stent graft will automatically expand and exert pressure on the wall of the blood vessel at the site of treatment. The guide wire may be used to perforate reduced yarn density regions to provide blood flow to branch vessels. The catheter, sleeve, and guide wire may then be removed from the patient.

In some examples, a bioabsorbable suture or sheath can be used to maintain a self-expanding stent graft in a compressed configuration both prior to and after deployment. As the bioabsorbable sheath or suture is degraded by the body after deployment, the prosthesis can expand within the body vessel. In some examples, a portion of the prosthesis can be restrained with a bioabsorbable material and another portion allowed to expand immediately upon implantation. For example, a self-expanding stent graft can be partially restrained by a bioabsorbable material upon deployment and later expand as the bioabsorbable material is absorbed.

In another example, a stent graft may be first positioned to surround a portion of an inflatable balloon catheter. The prosthesis, with the balloon catheter inside is configured at a first, collapsed diameter. The prosthesis and the inflatable balloon are percutaneously introduced into a body vessel, following a previously positioned guide wire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthesis are positioned within the body passageway at the point where the prosthesis is to be placed. Thereafter, the balloon is inflated and the prosthesis is expanded by the balloon portion from the collapsed diameter to a second expanded diameter. After the prosthesis has been expanded to the desired final expanded diameter, the balloon is deflated, reduced yarn density regions are perforated, and the catheter may be withdrawn, leaving the prosthesis in place. The prosthesis may be covered by a removable sheath during delivery to protect both the prosthesis and the vessels.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

We claim:

1. An implantable graft comprising:
   a main graft body forming a lumen with a proximal end and a distal end;
   where at least a portion of the lumen is defined by a woven fabric comprising yarns aligned in a first direction interwoven with yarns aligned in a second direction;
   where the woven fabric further comprises a main portion and at least one reduced yarn density region disposed between the proximal and distal end;
   where, although at least some yarns traverse the reduced yarn density region, the reduced yarn density region is defined by having a lower yarn density than the main portion; and
   where both the main portion and the reduced yarn density region are substantially impermeable to fluid flow.

2. The graft of claim 1, where the reduced yarn density region has between about 10% and about 90% fewer yarns aligned in the first direction than in the main portion.

3. The graft of claim 1, where the reduced yarn density region has between about 65% and about 85% fewer yarns aligned in the first direction than the main portion.

4. The graft of claim 1, where the at least one reduced yarn region comprises a first weave density about the circumference of the at least one reduced yarn density region and a second weave density about the center of the at least one reduced yarn density region, where the first weave density is more than the second weave density.

5. The graft of claim 1, where the yarns comprise a polymer selected from the group consisting of polyester, polypropylene, polyethylene, polyurethane, and polytetrafluoroethylene, and combinations thereof.

6. The graft of claim 4, where the polymer comprises polyester.

7. The graft of claim 1, where the reduced yarn density region is round, obround, polygonal, rectangular, square, or freeform, or combinations thereof.

8. The graft of claim 1, where the reduced yarn density region comprises a circumferential width which is less than the circumference of the lumen.

9. The graft of claim 1, where the yarns aligned in the first direction comprise warp yarns, and the yarns aligned in the second direction comprise weft yarns.

10. The graft of claim 9, where the main portion comprises between about 50 and about 300 weft yarns per inch and between about 50 and about 300 warp yarns per inch and where the reduced yarn density region comprises between about 10 and about 200 weft yarns per inch and between about 10 and about 200 warp yarns per inch.

11. The graft of claim 9, where the main portion comprises 150 weft yarns per inch and 250 warp yarns per inch and where the at least one reduced yarn density region comprises between about 20 and about 50 weft yarns per inch.

12. The graft of claim 1, further comprising at least one radiopaque element attached to the main graft body.

13. The graft of claim 12, where the at least one radiopaque element is located adjacent the reduced yarn density region.

14. An implantable prosthesis for treatment of a main vessel defect near one or more branch vessels, said prosthesis comprising:
   a graft comprising yarns aligned in a first direction interwoven with yarns aligned in a second direction, the woven yarns defining a lumen with a proximal end and a distal end, a main portion and at least one passage disposed between the proximal and distal end;
   where, although at least some yarns traverse the passage, the passage is defined by having a lower yarn density than the main portion; and
   where both the main portion and the passage are substantially impermeable to fluid flow.

15. The prosthesis of claim 14, further comprising at least two stents attached to the graft, one of which is attached between the distal end and the passage, the other of which is attached between the proximal end and the passage.

16. The prosthesis of claim 14, further comprising attachment mechanisms for securing the prosthesis within the main vessel selected from the group consisting of anchoring members, sutures, staples, searing, bonding, and bioadhesives, and combinations thereof.

17. The prosthesis of claim 14, further comprising a therapeutic agent adapted to be released from the prosthesis after implantation.

18. The prosthesis of claim 14, further comprising at least one radiopaque element for orienting the prosthesis within said main vessel.

19. The prosthesis of claim 15, further comprising a stent attached to the lumen distal end and stent attached to the lumen proximal end.

20. A method of bridging a defect in a main vessel near at least one branch vessel comprising:

providing a prosthesis comprising at least one stent and an implantable textile graft comprising yarns aligned in a first direction interwoven with yarns aligned in a second direction, said woven yarns defining a lumen with a main portion and at least one reduced yarn density region, wherein the reduced yarn density region has a yarn density lower than the main portion, where both the main portion and the reduced yarn density region are substantially impermeable to blood flow;

deploying the prosthesis into the main vessel of a patient in need thereof such that the reduced yarn density region is aligned with the at least one branch vessel;

perforating the at least one reduced yarn density region with a guidewire to define a passageway permitting blood flow from the main vessel to the at least one branch vessel.

* * * * *